United States Patent [19]
Johnson et al.

[11] 4,452,983
[45] Jun. 5, 1984

[54] PHENOLIC DERIVATIVE

[75] Inventors: James D. Johnson, St. Paul; Elden H. Banitt, Woodbury, both of Minn.

[73] Assignee: Riker Laboratories, Inc., St. Paul, Minn.

[21] Appl. No.: 439,637

[22] Filed: Nov. 5, 1982

Related U.S. Application Data

[63] Continuation of Ser. No. 271,254, Jun. 8, 1981, abandoned.

[51] Int. Cl.³ ............................................. C07D 211/26
[52] U.S. Cl. ..................................... 546/233; 424/267
[58] Field of Search ......................... 546/233; 424/267

[56] References Cited
U.S. PATENT DOCUMENTS 3,565,924  2/1971  DeLuca et al. ................. 260/397.2
3,655,728  4/1972  Mendel ........................... 260/473 R
3,715,374  2/1973  DeLuca ........................... 260/397.2
3,719,687  3/1973  Mendel ........................... 260/326.3
3,847,955  11/1974 DeLuca ........................... 260/397.2
3,900,481  8/1975  Banitt et al. ..................... 546/233
4,071,524  1/1978  Banitt ............................. 546/233
4,097,481  6/1978  Banitt et al. ..................... 546/233

OTHER PUBLICATIONS

E. H. Banitt et al., Jour. Med. Chem., (1977) vol. 20, No. 6 (1977), pp. 821–826.

Primary Examiner—Norma S. Milestone
Attorney, Agent, or Firm—Donald M. Sell; James A. Smith; Robert W. Sprague

[57] ABSTRACT

A novel N-(2-piperidylmethyl)-2,2,2-trifluoroethoxy)-benzamide and its pharmaceutically acceptable salts.

2 Claims, No Drawings

PHENOLIC DERIVATIVE

This is a continuation of Application Ser. No. 271,254 filed June 8, 1981 abandoned.

TECHNICAL FIELD

A novel N-(2-piperidylmethyl)-2,2,2-trifluoroethoxybenzamide and its pharmaceutically acceptable salts.

BACKGROUND OF THE INVENTION

Esters of benzoic acid substituted on the aromatic ring by 1,1-dihydroperfluoroalkoxy substituents are described in U.S. Pat. No. 3,655,728 and certain amides of benzoic acid substituted on the aromatic ring by 1,1-dihydroperfluoroalkoxy substituents are described in U.S. Pat. No. 3,719,687. U.S. Pat. Nos. 3,900,481, 4,071,524 and 4,097,481 describe antiarrhythmic agents including, inter alia, N-(piperidylmethyl)benzamides substituted by one or more 1,1-dihydroperfluoroalkoxy groups and an article appearing in the Journal of Medicinal Chemistry, Vol. 20, pg. 821 (1977), discloses many of the compounds of the patents, as well as various additional compounds. These include 2-(2,2,2-trifluoroethoxy)-N-(2-piperidylmethyl)benzamides in which the aromatic ring is substituted in the 5-position by a non-functional group, i.e. methyl, chloro of fluoro. These compounds are described to have reduced antiarrhythmic activity.

DISCLOSURE OF THE INVENTION

The present invention relates to 5-hydroxy-N-(2-piperidylmethyl)-2-(2,2,2-trifluoroethoxy)benzamide and its pharmaceutically acceptable salts. These compounds (the amide and its salts) include both a 2,2,2-trifluoroethoxy group and a phenolic hydroxy group bonded to the benzene ring. Unlike the compounds of the journal article discussed previously (which have a non-functional group bonded to the 5-position of the aromatic ring) they have been found to be useful antiarrhythmic agents.

The following diagram shows a method for the preparation of the amide of the invention, VIII.

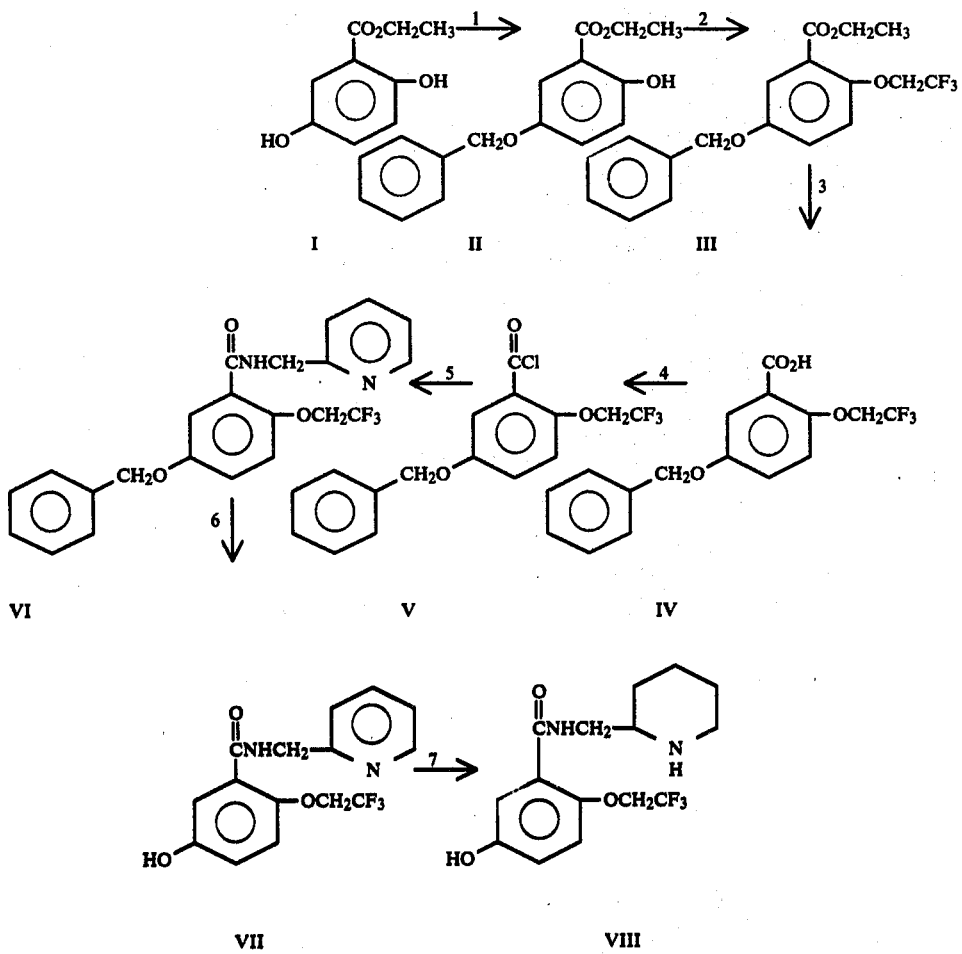

Thus, in Step 1 the ethyl ester of gentisic acid is reacted with benzyl chloride to selectively block the 5-hydroxy group. This reaction is carried out by heating the reactants in a suitable non-reactive solvent, such as acetone, in the presence of a weak inorganic base (sodium or potassium carbonate). The resulting solid II is recrystallized from hexane to provide a purified solid product with acceptable infrared and nuclear magnetic resonance spectra. The compound II is heated with 2,2,2-trifluoroethyl trifluoromethanesulfonate in a suitable nonreactive solvent, such as acetone, in the presence of a weak inorganic base (again, such as sodium or potassium carbonate) to provide the intermediate III. This compound is hydrolyzed by dissolving in a suitable solvent such as ethanol, adding aqueous sodium hydroxide (about 2 moles per mole of III) and heating at reflux. The product is a white solid, the intermediate 5-benzyloxy-2-(2,2,2-trifluoroethoxy)benzoic acid, IV.

In Step 4, the acid IV is converted to the corresponding acid chloride V by stirring with a suitable reagent such as thionyl chloride or, preferably, phosphorus pentachloride in a suitable nonreactive solvent such as benzene. The acid chloride is stirred with 2-aminomethylpyridine in a nonreactive solvent, such as chloroform, glyme, toluene, diethyl ether or benzene, in the presence of a weak organic base such as a tertiary amine or an inorganic base such as sodium or potassium carbonate. The resulting solid product is 5-benzyloxy-N-(2-pyridylmethyl)-2-(2,2,2-trifluroethoxy)benzamide, VI. This compound is debenzylated by dissolving it in a lower alkanol such as ethanol, adding palladium on charcoal as a catalyst and reacting with hydrogen gas. The novel phenolic product is 5-hydroxy-N-(2-pyridylmethyl)-2-(2,2,2-trifluoroethoxy)benzamide, VII.

In the final step of the process, the compound VII is catalytically reduced under acidic conditions to provide the amide compound of the invention VIII. Thus, VII is dissolved in a solvent such as acetic acid and reduced with hydrogen gas in the presence of platinum oxide catalyst. The resulting 5-hydroxy-N-(2-piperidylmethyl)-2-(2,2,2-trifluoroethoxy)benzamide acetate is readily converted to the free base VIII by reaction with a weak inorganic base such as sodium bicarbonate.

The compound of the invention can be used directly or in the form of pharmaceutically acceptable acid-addition salts, especially as the soluble acetic, hydrochloric, sulfuric or phosphoric acid salts. Other useful salts of the invention include hydrobromic acid, sulfamic acid, methanesulfonic acid, benzenesulfonic acid, ethanedisulfonic acid, citric acid, maleic acid, oxalic acid, succinic acid, malic acid, fumaric acid and tartaric acid salts. Pharmaceutically acceptable quaternary ammonium salts are also used, for example alkyl iodide and alkyl bromide salts, (especially lower alkyl in which the alkyl group contains not more than four carbon atoms).

The amide compound of the invention is active as an antiarrhythmic agent, as demonstrated in its ability to block chloroform-induced ventricular fibrillation in mice, in the test procedure described by J. W. Lawson, J. Pharmacol. Exp. Therap. 160:22-31, 1968.

In addition, the antiarrhythmic activity of this compound is shown by its ability to block ouabain-induced arrhythmias in anesthetized dogs (Lucchesi, B. R., Hardman, H. F.: The Influence of Dichloroisoproterenol (DCI) and Related Compounds Upon Ouabain and Acetylstrophanthidin Induced Cardiac Arrhythmias, J. Pharmacol. Exp. Ther. 132:373-381, 1961) and by its ability to block arrhythmias induced by coronary artery ligation in dogs (Harris, A. S.: Delayed Development of Ventricular Ectopic Rhythms Following Experimental Coronary Occlusion, Circ. 1:1318-1328, 1950).

In clinical practice, the compound of the invention will be normally administered as an antiarrhythmic orally or by injection in the form of pharmaceutical preparations comprising the active ingredient in the form of the free base or one of the common therapeutically acceptable salts, particularly the acetate or hydrochloride, in association with a pharmaceutically acceptable carrier. The carrier may be a solid, semi-solid or liquid diluent or an ingestible capsule. Usually the active substance will comprise between 0.01 percent and 5 percent of preparations intended for injection and between 10 percent and 80 percent of preparations intended for oral administration. Particularly preferred for intravenous use are 0.05-1.0 percent aqueous solutions of the active compounds buffered with sodium acetate to pH of about 5-7 and, for oral use, 20-60 percent formulations of the active ingredient in mannitol, lactose or potato starch.

Pharmaceutical preparations in the form of dosage units for oral administration containing the compound of the invention in the form of the free base or a pharmaceutically acceptable acid addition salt may be prepared in various ways. The compounds may be mixed with a solid, pulverulent carrier, for example lactose, saccharose, sorbitol, mannitol, starches such as potato starch, corn starch or amylopectin, cellulose derivatives, gelatin. The carrier may also be a lubricant such as magnesium or calcium stearate, a Carbowax or other polyethylene glycol wax compressed to form tablets, or, preferably, cores which are then coated with a concentrated sugar solution which may contain, e.g. gum arabic, gelatin, talcum and/or titanium dioxide.

Ingestible capsules which may be used include hard or soft gelatin capsules. Soft gelatin capsules (pearl-shaped closed capsules) and other closed capsules consist, for example, of a mixture of gelatin and glycerol, and contain, e.g. mixtures of the active substance with a vegetalbe oil, and hard gelatin capsules contain, for example, granulates of the active substance with solid, pulverulent carriers such as lactose, saccharose, sorbitol, mannitol; starches such as potato starch, corn starch, or amylopectin; cellulose derivatives or gelatin, as well as magnesium stearate or stearic acid.

For parenteral application by injection, the preparations of the invention advantageously comprise an aqueous, generally saline, solution of a water-soluble, pharmaceutically-acceptable salt of the active substance and optionally also a stabilizing agent and/or a buffer substance, e.g. sodium acetate.

The compound of the invention is also useful as a synthetic intermediate, e.g. for the preparation of flecainide (2,5-bis(2,2,2-trifluoroethoxy)-N-(2-piperidylmethyl)benzamide), and is known to be a metabolite when flecainide is administered to certain mammals.

DETAILED DESCRIPTION

The following examples more fully illustrate the preparation of the compound of the invention. All temperatures in the examples given are in degrees Centigrade.

EXAMPLE 1

In 100 ml of acetone is dissolved 15 g (0.0824 moles) of ethyl 2,5-dihydroxybenzoate, 13.9 g (0.110 mole) benzyl chloride and 34.1 g (0.247 mole) potassium carbonate. The mixture is heated to its reflux temperature and maintained at reflux for 22 hours. The solution is filtered and the residue is washed with acetone. The filtrate and washings are concentrated, and the residue is dissolved in diethyl ether. The ether extracts are washed twice with water then with saturated sodium chloride solution and finally dried over magnesium sulfate. The magnesium sulfate is removed by filtration and the solution is evaporated to provide a suspension of product which is triturated with hexane and dried to provide a solid. The solid is recrystallized from hexane to provide ethyl 5-benzyloxy-2-hydroxybenzoate, m.p. 71.5°-73° C.

EXAMPLE 2

To a refluxing mixture of 100 ml of acetone, 10.3 g (0.0379 mole) of ethyl 5-benzyloxy-2-hydroxybenzoate and 10.5 g (0.0757 mole) of potassium carbonate is added dropwise over about 1 hour 13.2 g (0.0568 mole) 2,2,2-trifluoroethyl trifluoromethanesulfonate. The mixture is heated at reflux for another 16 hours then evaporated to provide a residue which is dissolved in water and diethyl ether. The layers are separated and the ether is washed with water, then saturated sodium chloride solution and dried over magnesium sulfate. The magnesium sulfate is removed by filtration and the diethyl ether is removed by evaporation to provide the product, ethyl 5-benzyloxy-2-(2,2,2-trifluoroethoxy)-benzoate. The infrared spectrum of this material is consistent with the assigned structure.

EXAMPLE 3

To a solution of ethyl 5-benzyloxy-2-(2,2,2-trifluoroethoxy)benzoate (13.3 g obtained from the reaction of Example 2) in 100 ml of ethanol is added 3.0 g of sodium hydroxide dissolved in 100 ml of water. The mixture is heated at its reflux temperature for about 16 hours then cooled, filtered and ethanol is removed from the filtrate by evaporation. The residue from the evaporation is diluted with water and acidified with concentrated hydrochloric acid and the mixture is filtered to separate the white solid product, 5-benzyloxy-2-(2,2,2-trifluoroethoxy)benzoic acid, m.p. 145°–146° C.

EXAMPLE 4

To a suspension of 9.3 g (0.0285 mole) of 5-benzyloxy-2-(2,2,2-trifluoroethoxy)benzoic acid in 140 ml of benzene is added 6.1 g (0.0294 mole) potassium pentachloride. The solution is stirred at room temperature for about 16 hours then is concentrated to an oil, which crystallizes gradually. The infrared spectrum of this material is consistent with the structure of the desired product, 5-benzyloxy-2-(2,2,2-trifluoroethoxy)benzoyl chloride.

EXAMPLE 5

To a solution of 3.2 g (0.0299 mole) of 2-aminomethylpyridine and 12.1 g (0.114 mole) of sodium carbonate in 100 ml of benzene is added dropwise a solution of 9.8 g (0.0285 mole) of 5-benzyloxy-2-(2,2,2-trifluoroethoxy)benzoyl chloride in 30 ml benzene. The mixture is stirred for about 16 hours at room temperature. Water and diethyl ether are added. The ether layer is separated, washed with water, then with saturated aqueous sodium chloride solution. The solution is dried over magnesium sulfate, and the magnesium sulfate is removed by filtration. The filtrate is evaporated to provide a white solid, 5-benzyloxy-N-(2-pyridylmethyl)-2-(2,2,2-trifluoroethoxybenzamide. The infrared and nuclear magnetic resonance spectra of this product are consistent with the assigned structure.

EXAMPLE 6

A mixture of 11.8 g (0.0285 mole) of 5-benzyloxy-N-(2-pyridylmethyl)-2-(2,2,2-trifluoroethoxy)benzamide, 1.0 g of palladium on charcoal and 250 ml of ethanol is shaken in a Parr apparatus while hydrogenating with hydrogen gas. The catalyst is removed by filtration and the filtrate is concentrated to provide an amorphous white solid. The solid is diluted with fresh ether, then concentrated again to provide 8.4 g of a white solid. The infrared and nuclear magnetic resonance spectra of this product are consistent with the structure of 5-hydroxy-2-(2,2,2-trifluoroethoxy)-N-(2-pyridylmethyl)-benzamide.

EXAMPLE 7

The crude product from Example 6 is mixed with 0.3 g of platinum oxide in 250 ml of glacial acetic acid. The mixture is reduced with hydrogen gas in a Parr apparatus. The catalyst is removed by filtration and the filtrate is evaporated to provide a solid residue. This product, 5-hydroxy-N-(2-piperidylmethyl)-2-(2,2,2-trifluoroethoxy)benzamide acetate, is dissolved in water and the aqueous solution is basified with sodium bicarbonate solution. The water solution is then extracted with a large volume of dichloromethane and the dichloromethane extracts are dried over magnesium sulfate. The magnesium sulfate is removed by filtration and the solvent is evaporated to provide a solid product. The product is recrystallized from toluene, treated with charcoal, filtered and rinsed with a toluene-hexane mixture. Another recrystallization from a 1:1 mixture of toluene and hexane provides tan needles of 5-hydroxy-2-(2,2,2-trifluoroethoxy)-N-(2-piperidylmethyl)benzamide, m.p. 134°–137° C.

| Analysis: | % C | % H | % N |
| --- | --- | --- | --- |
| Calculated for $C_{15}H_{19}F_3N_2O_3$: | 54.2; | 5.8; | 8.4; |
| Found: | 54.2; | 5.8; | 8.1 |

What is claimed is:

1. Synthetic 5-hydroxy-2-(2,2,2-trifluoroethoxy)-N-(2-piperidylmethyl)benzamide or a pharmaceutically acceptable salt thereof.

2. Substantially pure 5-hydroxy-2-(2,2,2-trifluoroethoxy)-N-(2-piperidylmethyl)benzamide or a pharmaceutically acceptable salt thereof.

* * * * *